(12) United States Patent
Chen et al.

(10) Patent No.: US 7,967,750 B2
(45) Date of Patent: Jun. 28, 2011

(54) LIE DETECTION VIA ELECTROGASTROGRAPHY

(75) Inventors: Jiande Chen, Houston, TX (US);
Pankaj J. Pasricha, Houston, TX (US);
Trisha Pasricha, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1016 days.

(21) Appl. No.: 11/787,081

(22) Filed: Apr. 13, 2007

(65) Prior Publication Data

US 2008/0177157 A1    Jul. 24, 2008

Related U.S. Application Data

(60) Provisional application No. 60/791,863, filed on Apr. 13, 2006.

(51) Int. Cl.
*A61B 5/00*    (2006.01)

(52) U.S. Cl. ........... 600/300; 600/301; 600/509; 607/40
(58) Field of Classification Search ................... None
See application file for complete search history.

(56) References Cited

OTHER PUBLICATIONS

Hutson, Stu. (2005). "Gut Reactions May Rumble a Liar." NewScientist.com Breaking News, October 31.*

* cited by examiner

*Primary Examiner* — Henry M Johnson, III
*Assistant Examiner* — Kai Rajan
(74) *Attorney, Agent, or Firm* — Benjamin Aaron Adler

(57) ABSTRACT

The present invention provides a device and methods of lie detection utilizing electrogastrography to monitor changes in the gastric electric rhythm of a subject. Also provided are methods of discriminating between the stress of deception induced in a subject during a lie detection examination and the stress of the examination itself.

7 Claims, No Drawings

LIE DETECTION VIA ELECTROGASTROGRAPHY

CROSS-REFERENCE TO RELATED APPLICATIONS

This nonprovisional application claims benefit of provisional U.S. Ser. No. 60/791,863, filed Apr. 13, 2006, now abandoned.

BACKGROUND OF THE INVENTION

1. Field of the Invention

The present invention relates generally to the fields of polygraphs and lie detection. More specifically, the present invention relates to a method of lie detection utilizing electrogastrography.

2. Description of the Related Art

Lie detection by objective means is desired in several circumstances including criminal investigations and pre-employment screening for high-security positions. Additionally, many government entities and some private-sector employers may require or may ask potential employees to undergo a polygraph exam prior to employment. Currently, this is accomplished by a polygraph examination that utilizes a polygraph instrument that collects physiological data from at least three systems in the human body. A polygraph instrument detects involuntary physiological responses going on in a person's body when that person is subjected to stress, including the stress of deception. Responses monitored during a polygraph examination, traditionally including heart rate, blood pressure, respiratory rate and electrodermal activity, e.g., the galvanic skin response which can be measured in the sweatiness of a fingertip, change in comparison to normal levels.

Most polygraph tests are of the CQT variety in which deception is determined by comparing physiological responses to relevant questions to a baseline determined by control questions. A typical polygraph examination a pre-test phase, a chart collection phase and a test data analysis phase. In the pre-test, the polygraph examiner completes required paperwork and talks with the examinee about the test. The examiner discusses the questions to be asked and familiarizes the examinee with the testing procedure. During the chart collection phase, the examiner administers and collects a number of polygraph charts. The examiner subsequently analyzes the charts and renders his opinion as to the truthfulness of the person taking the test. When appropriate, the examiner may offer the examinee an opportunity to explain physiological responses in relation to one or more questions asked during the test.

A system for lie detection is only as good as its ability to discriminate between the stress of deception or lying and the simple stress engendered by the polygraph examination itself. Thus, when the Examiner administers the relevant questions, the fact that the examinee is being questioned, that is, the actual polygraph examination has commenced, may be sufficient to elevate anxiety levels in the examinee from baseline even when the examinee is responding truthfully. Additionally, artificially inflated baseline values to control questions may be acquired when the examinee employs physical or mental countermeasures to beat the polygraph. In this instance deceptive response may score even with or lower than baseline.

Electrogastrography describes the recording and interpretation of electrical activity of the stomach. Recordings can be made from the gastrointestinal mucosa, serosa, or skin surface. Because of its ease of use, cutaneous EGG is used most frequently. The electrical activity of the stomach can be subdivided into two general categories: electrical control activity (ECA) and electrical response activity (ERA). Electrical control activity is characterized by regularly recurring electrical potentials, originating in the gastric pacemaker located in the corpus of the stomach and sweeping in an annular band with increasing velocity toward the pylorus. Electrical control activity is not associated with contractions of the stomach unless coupled with action potentials, referred to as electrical response activity.

There is a recognized need in the art for improvements in systems and methods for lie detection. Specifically, the prior art is deficient in devices and methods that measure the gastric electrical rhythm as a parameter in lie detection. The present invention fulfills this long-standing need and desire in the art.

SUMMARY OF THE INVENTION

The present invention is directed to a device for lie detection. The device has a means for measuring involuntary heart rate variability (HRV), a means for measuring gastric electric rhythm and a processing unit operatively connected to the means for recording the heart rate variability and the gastric electric rhythm. The processing unit configured to record the measurements and to utilize the recorded measurements to (i) determine a baseline level of physiological response for both heart rate variability and gastric electric rhythm for a plurality of control questions; (ii) determine a change in the physiological responses from baseline for each question of a plurality of relevant questions; and (iii) process the changes in physiological response to identify truthfulness or lack thereof of a response to each relevant question.

The present invention also is directed to a method for evaluating the truthfulness of a subject. The method requires posing a plurality of control questions to the subject and posing a plurality of relevant questions to the subject and determining heart rate variability and gastric electric rhythm in the subject after posing the controlling questions to obtain a baseline for each of the heart rate variability and gastric electric rhythm. Heart rate variability and gastric electric rhythm in the subject is determined after posing the relevant questions. The heart rate variability and the gastric electric rhythm after posing the relevant questions are compared with the heart rate variability baseline and the gastric electric rhythm baseline such that an occurrence of bradygastria during posing of the relevant questions compared to the corresponding baseline is indicative of truthfulness, even if heart rate variability increases compared to its corresponding baseline during posing of the relevant questions.

The present invention is directed further to a method of discriminating between stress of deception induced in a subject during a polygraph test and stress induced from the polygraph test itself. A polygraph test is administered to the subject during which gastric electric rhythm and another involuntary physiological response, comprising at least heart rate variability, that occur when a plurality of control questions and a plurality of relevant questions are posed to the subject are recorded. A physiological change in a gastric electric rhythm from baseline level is compared with a physiological change in heart rate variability from its baseline level whereby a bradygastric change with an increase in heart rate variability is indicative of stress induced from the polygraph test itself and a tachygastric change with an increase in heart rate variability is indicative of stress induced from deception.

The present invention is directed further still to a method of improving the accuracy of lie detection during a polygraph test of an individual. The method comprises monitoring heart rate variability during administration of the polygraph test and monitoring concurrently a gastric electric rhythm of the individual. A change in gastric electric rhythm is indicative of a truthful or of a false response even if an increase in heart rate variability sufficient to indicate a false response is detected, thereby improving the accuracy of lie detection during the polygraph examination. The present invention is directed to a related method comprising monitoring independently one or more involuntary responses of respiration rate, blood pressure or galvanic skin response during administration of the polygraph test.

Other and further aspects, features, and advantages of the present invention will be apparent from the following description of the presently preferred embodiments of the invention. These embodiments are given for the purpose of disclosure.

DETAILED DESCRIPTION OF THE INVENTION

In one embodiment of the present invention there is provided a device for lie detection, comprising means for measuring involuntary heart rate variability; means for measuring gastric electric rhythm; and a processing unit operatively connected to the means for measuring the heart rate variability and the gastric electric rhythm; where the processing unit is configured to record the measurements and to utilize the recorded information so as to (i) determine a baseline level of physiological response for both heart rate variability and gastric electric rhythm for a plurality of control questions; (ii) determine a change in the physiological responses from baseline for each question of a plurality of relevant questions; and (iii) process the changes in physiological response to identify truthfulness or lack thereof of a response to each relevant question.

In this embodiment the device further may comprise a means for recording independently an additional one or more involuntary physiological response. Examples of the involuntary physiological responses may be respiration rate, blood pressure or galvanic skin response or a combination thereof. In one aspect of these embodiments the heart rate variability is measured by an electrocardiograph. In another aspect the gastric electric rhythm is measured by an electrogastrograph. In all aspects of these embodiments the device may comprise a polygraph instrument.

In another embodiment of the present invention there is provided a method for evaluating the truthfulness of a subject, comprising posing a plurality of control questions to the subject; posing a plurality of relevant questions to the subject; determining heart rate variability and gastric electric rhythm in the subject after posing the controlling questions thereby determining a baseline for each of the heart rate variability and gastric electric rhythm; determining heart rate variability and gastric electric rhythm in the subject after posing the relevant questions; and comparing the heart rate variability and gastric electric rhythm generated after posing the relevant questions with the heart rate variability baseline and the gastric electric rhythm baseline; wherein an occurrence of bradygastria during posing of the relevant questions compared to the corresponding baseline is indicative of truthfulness even if heart rate variability increases compared to its corresponding baseline during posing of the relevant questions.

In this embodiment the method further may comprise a step of independently determining an additional one or more involuntary physiological responses in the subject after posing said controlling and said relevant questions. In aspects of this further embodiment the involuntary physiological response may be respiration rate, blood pressure or galvanic skin response or a combination thereof.

In all aspects of these embodiments, posing the control questions and the relevant questions may occur during a polygraph test. In one aspect of these embodiments determining heart rate variability is via electrocardiography. In another aspect determining the gastric electric rhythm is via electrogastrography. Further to these aspects the occurrence of bradygastria with the increase in heart rate variability from baseline is indicative of stress in the subject induced by posing said relevant questions. In a related aspect an occurrence of tachygastria with the increase in heart rate variability from baseline is indicative of stress in the subject induced by deception in responding to the relevant questions.

In yet another embodiment of the present invention there is provided a method of discriminating between stress of deception induced in a subject during a polygraph test and stress induced from the polygraph test itself, comprising administering a polygraph test to the subject comprising recording a gastric electric rhythm and another involuntary physiological response comprising at least heart rate variability that occur when a plurality of control questions and a plurality of relevant questions are posed to the subject; comparing a physiological change in a gastric electric rhythm from a baseline level with a physiological change in heart rate variability from baseline, where a bradygastric change with an increase in heart rate variability is indicative of stress induced from the polygraph test itself and a tachygastric change with an increase in heart rate variability is indicative of stress induced from deception.

In still another embodiment of the present invention there is provided a method of improving the accuracy of lie detection during a polygraph test of an individual, comprising monitoring heart rate variability during administration of the polygraph test; and monitoring concurrently a gastric electric rhythm of the individual, wherein a change in gastric electric rhythm is indicative of a truthful or of a false response even if an increase in heart rate variability sufficient to indicate a false response is detected, thereby improving the accuracy of lie detection during the polygraph test. In a further embodiment the method provides monitoring independently one or more involuntary responses of respiration rate, blood pressure or galvanic skin response during administration of the polygraph test.

In one aspect of this embodiment a bradygastric change in gastric electric rhythm with the increase in heart rate variability is indicative of a truthful response. In an alternative aspect a tachygastric change in gastric electric rhythm with the increase in heart rate variability is indicative of a false response.

Further to this embodiment the method may comprise recording independently one or more involuntary responses of respiration rate, blood pressure or galvanic skin response. In one aspect of these embodiments the recording the heart rate variability is via an electrocardiograph. In another aspect recording the gastric electric rhythm is via an electrogastrograph.

As used herein, the term, "a" or "an" may mean one or more. As used herein in the claim(s), when used in conjunction with the word "comprising", the words "a" or "an" may mean one or more than one. As used herein "another" or "other" may mean at least a second or more.

As used herein, the term "polygraph" refers to any kind of lie detector, typically, to an instrument for recording physiological phenomena such as blood pressure, pulse or heart rate, respiration and, optionally, a galvanic skin response of a subject as the subject listens and responds to questions put to him by an operator. The recorded data are then used as the basis for making a judgment as to whether or not the subject is lying. As is well recognized in the art, the terms "polygraph" and "lie detector" are used interchangeably.

As used herein, the phrase "control question" refers to a question to which the subject will lie, or at the very least, a question that causes a disturbance in the subject. For example, in polygraphing potential or existing employees a standard control question is "Have you ever stolen prior to working for this company?". Irrelevant questions, based on true and obvious statements of fact also are asked, such as the name and address of the subject or about known facts in the life of the subject. A "relevant question" is any question designed to elicit specific information from the subject relevant to the situation for which the polygraph is being administered and to evaluate the truthfulness of the subject in responding to the relevant question.

As used herein, the term "subject" refers to any individual participating in a polygraph or lie detector test.

As used herein, "sympathovagal balance" refers to a characterization of the autonomic state resulting from sympathetic and vagal or parasympathetic influences which can be associated with heart rate variability. It is well known in the art that conditions, e.g., mental stress, assuming an upright position and exercise are associated with an increase of sympathetic tone. In contrast vagal or parasympathetic tone is high during resting or less or minimally stressful conditions.

As used herein "bradygastria" or "bradygastric change" refers to a gastric electric rhythm that is too slow or slower than or slowed down from a normogastric or baseline or control measurement of gastric electric rhythm.

As used herein "tachygastria" or "tachygastric change" refers to a gastric electric rhythm that is too fast or faster than or increased from a normogastric or baseline measurement or control of gastric electric rhythm.

Provided herein are devices and methods for lie detection utilizing electrogastrography (EGG) to measure the gastric electric rhythm of a subject undergoing a polygraph or lie detector test. The change in the gastric electric rhythm measured by electrogastrography can be used to distinguish lying from truth and from baseline measures acquired prior to administration of the polygraph or lie detection test. The devices and methods of the present invention may be used to improve existing devices, systems and methods for lie detection by adding another parameter, the gastric electric rhythm, to the battery of involuntary physiological responses previously monitored. This not only increases the overall accuracy by increasing the number of variables being measured, but also is better able to discriminate simple stress induced by the polygraph or lie detection examination itself from the specific stress of lying.

As such the device of the present invention may comprise a polygraph instrument having means to measure at least heart rate variability and one or more of respiration rate, blood pressure or galvanic skin response or a combination thereof or other physiological response suitable for a polygraph process in a subject. Heart rate variability and other involuntary physiological responses may be measured by those means standard in the art. For example, in the present invention heart rate variability is measured via electrocardiography. Gastric electric rhythm is measured via electrogastrography.

The device further comprises a processing unit configured to record and compare physiological responses. As is standard and known in the art, the processing unit is designed to determine baseline physiological response levels for control questions and to record changes in physiological levels when relevant questions are posed to the subject. The processing unit is suitable to be configured to record baseline levels and changes in the gastric electric rhythm occurring when control and relevant questions are posed to the subject.

The truthfulness of a subject may be evaluated by posing control and relevant questions and comparing the control physiological response with the relevant physiological response. A decrease in gastric electric rhythm or bradygastria is an indicator of truthfulness even with an increase in heart rate variability over baseline. Such comparison may be used to differentiate between the stress induced in a subject from deceptive answers and the stress induced in the subject, even if the subject is being truthful, caused from taking the polygraph test itself. Alternatively, a measurable increase in both gastric electric rhythm, i.e., tachygastria, and heart rate variability is indicative of stress induced by deception.

The following example(s) are given for the purpose of illustrating various embodiments of the invention and are not meant to limit the present invention in any fashion.

Example 1

Comparison of EGG with ECG During Lie Detection

Fourteen healthy volunteers (11 female and 3 male) with a mean age of 39.2±3 years were recruited. Simultaneous electrogastrography and ECG recordings were made. The recordings were 1) Baseline Period: a 10 min recording of baseline; 2) Lying Period: a 6 min period of lying followed by a 3 min rest period; and 3) Truth Period: a 6 min period of truth followed by a 3 min rest period. Lying and truth periods were introduced randomly to subjects. One female subject was excluded as she experienced a severe attack of cough that disturbed both the electrogastrography and the ECG tracings. To detect differences between each two periods, Student t-test was performed. Analysis of variance (ANOVA) was done to detect differences among all three groups. P value was set at <0.05.

The first channel of electrogastrography, located on the stomach pacemaker area, showed a tendency to decrease in the percentage of normal slow wave in lying compared with both baseline and truth periods (73.8±6.6 vs. 85.9±4.4 and 85.6±6.6; P=0.07 and 0.07, respectively). This may be attributed to the tendency of increase in the percentage of tachygastria in lying versus baseline in the same channel (6.9±3 vs. 3.1±1.7; P=0.08).

Spectral analysis of the heart rate variability (HRV) signal derived from the EECG recording showed an increase in the average heart rate in lying and truth versus baseline (75.28±2.1 and 74.26±2 vs. 71.88±1.7) showing a statistical difference between baseline and lying (P=0.01), baseline and truth (P=0.01), but not between lying and truth (P=0.19).

There was a significant increase in the sympathovagal balance in both lying and truth periods in comparison to baseline (1.33±0.16 and 1.59±0.27 vs. 0.94±0.10; P=0.02 and 0.01, respectively). There was a marginal statistical difference between all three groups detected by ANOVA, i.e., P=0.07. This increase in the sympathovagal balance might be attributed to the significant decrease in the vagal activity in both lying and truth periods in comparison to baseline (0.34±0.04 and 0.34±0.04 vs. 0.42±0.04; P=0.04 and 0.004, respectively).

One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for evaluating the truthfulness of a subject's response to questions posed during administration of a polygraph examination thereto, comprising:
    connecting the subject to a polygraph instrument comprising:
        channels for measurement of heart rate variability via electrocardiography and gastric electric rhythm via gastroelectrography; and
        a processing unit operatively connected thereto; said processing unit configured to record and compare the measurements;
    posing a plurality of control questions to the subject;
    posing a plurality of relevant questions to the subject;
    measuring heart rate variability and gastric electric rhythm in the subject after posing the controlling questions to obtain a baseline for each of said heart rate variability and gastric electric rhythm;
    measuring heart rate variability and gastric electric rhythm in the subject after posing the relevant questions; and
    comparing the heart rate variability and gastric electric rhythm after posing said relevant questions with the heart rate variability baseline and the gastric electric rhythm baseline, wherein an occurrence of bradygastria during posing of said relevant questions compared to the corresponding baseline is indicative that the response to the relevant questions is truthful even if heart rate variability increases compared to its corresponding baseline during posing of said relevant questions.

2. The method of claim 1, further comprising:
    measuring independently an additional one or more involuntary physiological responses in the subject after posing said controlling and said relevant questions.

3. The method of claim 2, wherein said involuntary physiological response is respiration rate, blood pressure or galvanic skin response or a combination thereof.

4. The method of claim 1, wherein said occurrence of bradygastria with said increase in heart rate variability from baseline is indicative of stress in the subject induced by posing said relevant questions.

5. The method of claim 1, wherein an occurrence of tachygastria with said increase in heart rate variability from baseline is indicative of stress in the subject induced by deception in responding to said relevant questions.

6. A method of improving the accuracy of lie detection during a polygraph examination of a subject, comprising:
    connecting the subject to a polygraph instrument comprising:
        channels for monitoring heart rate variability via electrocardiography and gastric electric via a gastroelectrography; and
        a processing unit operatively connected thereto said processing unit configured to record and compare heart rate variability and gastric electric rhythm:
    monitoring heart rate variability during administration of the polygraph examination; and
    monitoring concurrently a gastric electric rhythm of the individual, wherein a bradygastric change in gastric electric rhythm is indicative of a truthful response from the subject even if an increase in heart rate variability sufficient to indicate a false response is detected and a tachygastric change in gastric electric rhythm with said increase in heart rate variability is indicative of a false response, thereby improving the accuracy of lie detection during the polygraph examination.

7. The method of claim 6, further comprising:
    monitoring independently one or more involuntary responses of respiration rate, blood pressure or galvanic skin response.

* * * * *